(12) United States Patent
Cayuela et al.

(10) Patent No.: US 7,183,108 B1
(45) Date of Patent: Feb. 27, 2007

(54) SELECTION AND USES OF LACTIC ACID BACTERIA STRAINS MODULATING NON-SPECIFIC IMMUNITY

(75) Inventors: Chantal Cayuela, Paris (FR); Nathalie Dugas, Verrieres-le-Buisson (FR); Eric Postaire, Vanves (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 09/856,969

(22) PCT Filed: Nov. 18, 1999

(86) PCT No.: PCT/FR99/02826

§ 371 (c)(1),
(2), (4) Date: Aug. 1, 2001

(87) PCT Pub. No.: WO00/28943

PCT Pub. Date: May 25, 2000

(30) Foreign Application Priority Data

Nov. 18, 1998 (FR) ................................. 98 14471

(51) Int. Cl.
*C12N 5/06* (2006.01)
*C12N 5/00* (2006.01)
*C12N 1/20* (2006.01)
*C12P 21/04* (2006.01)
*C12Q 3/00* (2006.01)

(52) U.S. Cl. ..................... 435/375; 423/374; 423/405; 424/93.45; 424/152.1; 424/153; 424/157.1; 424/178.1; 424/278.1; 435/3; 435/69.51; 435/69.52; 435/69.6; 435/252.9; 435/335; 435/337; 435/340; 435/343; 435/375; 436/9; 436/106; 436/116; 436/543; 436/815; 530/351; 530/365; 530/380; 530/388.23; 530/388.7; 530/388.73; 530/389.2

(58) Field of Classification Search ............... 435/7, 435/7.32, 37, 38, 40.5, 41, 120, 139, 152, 435/170, 3, 69.51, 69.52, 69.6, 252.9, 335, 435/337, 340, 343, 375; 530/319, 351, 365, 530/380, 388.23, 388.7, 388.73, 389.2; 562/589; 930/200; 424/93.45, 152.1, 153, 157.1, 178.1, 424/278.1, 153.7; 423/374, 405
See application file for complete search history.

(56) References Cited

U.S. PATENT DOCUMENTS 5,032,399 A     7/1991 Gorbach et al.

(Continued)

FOREIGN PATENT DOCUMENTS

DE      2126071     *  9/1992

(Continued)

OTHER PUBLICATIONS

Thomas Witthölf, Lars Eckmann, Jung Mogg Kim, Martin F. Kagnoff; *Enteroinvasive bacteria directly activate expression of iNOS and NO production in human colon epithelial cells*; American Journal of Physiology: Gastrointestinal and Liver Physiology; American Physiological Society; Sep. 1998; pp. G564-G571; vol. 38, No. 3; XP-002115076; Washington, DC, US.

(Continued)

*Primary Examiner*—Lynette R. F. Smith
*Assistant Examiner*—J. Hines
(74) *Attorney, Agent, or Firm*—Alston & Bird LLP

(57) ABSTRACT

The invention concerns lactic acid bacteria strains capable of regulating the production of NO and inflammatory cytokines by enterocytes, depending on the inflammatory condition of said enterocytes. The strains can also be incorporated in food supplements such as fermented dairy products used for regulating inflammatory response and non-specific immunity.

9 Claims, 4 Drawing Sheets

U.S. PATENT DOCUMENTS

| | | | |
|---|---|---|---|
| 5,413,785 A | 5/1995 | Nanji | |
| 5,591,428 A | 1/1997 | Bengmark et al. | |
| 5,716,615 A | 2/1998 | Cavaliere Vesely et al. | |
| 6,399,055 B1* | 6/2002 | Postaire et al. | 424/93.45 |
| 6,444,203 B2* | 9/2002 | Krueger et al. | 424/93.44 |

FOREIGN PATENT DOCUMENTS

| | | | |
|---|---|---|---|
| EP | WO 88/ 00438 | * | 1/1988 |
| EP | 0 199 535 A2 | | 10/1996 |
| EP | 0 794 707 B1 | | 9/1997 |
| EP | 0 861 905 A2 | | 9/1998 |
| FR | WO 96/20607 | * | 6/1996 |
| WO | WO 96/20607 | | 7/1996 |
| WO | WO 98/06411 | | 2/1998 |
| WO | WO 98/27991 | | 7/1998 |

OTHER PUBLICATIONS

Eric Postaire, Bernard Dugas, Chantal Cayuela, Purificacion Relano, Nathalie Dugas; *Role of Nitric Oxide in the Muscosal Immuno-Regulatory Properties of Probiotic Strains*; FASEB Journal for Experimental Biology; Mar. 12, 1999; p. A291; vol. 13, No. 4; XP002137007; Bethesda, MD, US.

Tuomola et al., "Adhesion of some probiotic and dairy *Lactobacillus* strains to Caco-2 cells cultures", *International Journal of Food Microbiology*, 41 (1998) pp. 45-51.

Yeung et al., "Species-Specific Indentification of Commercial Probiotic Strains", *American Diary Science Association*, vol. 85, No. 5, 2002, pp. 1039-1051.

Majamaa et al., "Lactic Acid Bacterial in the Treatment of Acute Rotavirus Gastroenteritis", *Journal of Pediatric Gastroenterology and Nutrition*, 1995, pp. 333-338.

Miettinen et al., "Production of Human Tumor Necrosis Factor Alpha, Interleukin-6, and interleukin-10 is Induced by Lactic Acid Bacteria", *Infection and Immunity, American Society for Microbiology*, Dec. 1996. pp. 5403-5405.

Collins, et al., "Deoxyribonucleic Acid Homology Studies of *Lactobacillus casei*, *Lactobacillus paracasei* sp. Nov., subsp. *Paracasei* and subsp. *tolerans*, and *Lactobacillius rhamnousus* sp. Nov., comb. Nov." *International Journal of Systematic Bacteriology*, Apr. 1989, pp. 105-108.

Kaila et al., "Viable versus inactivated lactobacillus strain GG in acute rotavirus diarrhea", *Archives of Disease in Childhood*, 1995, pp. 51-53.

Perdigon et al., "Immunoadjuvant activity of oral *Lactobacillus casei*: influence of dose on the secretory immune response and protective capacity in intestinal infections", *Journal of Dairy Research* (1991), pp. 485-496.

Shibolet, et al., "Variable Response to Probiotics in Two Models of Experimental Colitis in Rats", *Inflammatory Bowel Diseases*, 2002, pp. 399-406.

VSL #3 product information, www.vslpharma.com.

Isolauri et al., "Oral Bacteriotherapy for Viral Gastroenteritis", *Digestive Diseases and Sciences*, vol. 39. No. 12 (Dec. 1994), pp. 2595-2600.

Majamaa et al., "Probiotics: A novel approach in the mangagement of food allergy", *J. Allergy Clin. Immunol*, vol. 99, No. 2, 179-185.

Biller, et al., "Treatment of Recurrent *Clostridium difficile* Colitis With *Lactobacillus GG*", *Journal of Pediatric Gastroenterology and Nutrition*, 1995, 224-226.

Malin et al., "Promotion of IgA Immune Response in Patients with Crohn's Disease by Oral Bacteriotherapy with *Lactobacillus GG*", *Ann Nutr Metab.*, 1996, pp. 137-145.

Pelto et al., "Probiotic bacterial down-regulate the mild-induced inflammatory response in milk-hypersensitive subjects but have an immunostimulatory effect in healthy subjects", *Clinical and Experimental Allergy*, 1998, vol. 28, pp. 1474-1479.

Korhonen et al., "Induction of Nitric Oxide Synthesis by Probiotic *Lactobacillus rhamnosus* GG in J774 Macrophages and Human T84 Intestinal Epithelial Cells", *Inflammation*, vol 25. No. 4, Aug. 2001, pp. 223-232.

Isolauri et al., "Probiotics: effects on immunity", *Am J Clin Nutr*, 2001, 73 (suppl) pp. 444S-450S.

Blacklow et al., "Viral Gastroenterits Agents", *Viruses, Rickettsiae, and Chlamydiae*, pp. 805-812.

Dugas et al., "Regulation by Endogenous Interleukin-10 of the Expression of Nitric Oxide Synthase Induced After Ligation of CD23 in Human Macrophages", *Cytokine*, vol. 10, No. 9 Sep. 1998, pp. 680-689.

Rachimilewitz et al., "Enhanced colonic nitric oxide generation and nitric oxide synthase activity in ulcerative colitis and Crohn's disease", *NO generation for IBD*, 1995, pp. 718-723.

Rachmilewitz et al., "Experimental colitis is ameliorated by inhibition of nitric oxide synthase activity", *Gut*, 1995, 37, pp. 247-255.

Kolios et al., "Expression of inducible nitric oxide synthase activity in human colon epithelial cells: modulation by T lymphocyte derived cytokines", *Gut*, 1998, 43, pp. 56-63.

Alvarez et al., "Immune system stimulation by probiotics", *J Dairy Sci.*, Jul. 1995, 78(7), pp. 1597-1606.

Perdigon et al., "Systemic augmentation of the immune response in mice by feeding fermented milks with *Lactobacillus casei* and *Lactobacillus acidophilus*", *Immunology*, 1988, 63, pp. 17-23.

Tejada-Simon et al., "Ex Vivo Effects of *Lactobacilli, Streptococci, and Bifidobacteria* Ingestion on Cytokine and Nitric Oxide Production in a Murine Model", *Journal of food Protection*, vol. 62, No. 2, 1999, pp. 162-169.

Alican et al., "A critical role for nitric oxide in intestinal barrier function and dysfunction", *American Physiological Society*, 1996, pp. G225-G237.

Tepperman et al., "Nitric Oxide Synthase Activity, Viability and Cyclic GMP Levels in Rat Colonic Epithelial Cells: Effect of Endotoxin Challege", *The Journal of Pharmacology and Experimental Therapeutics*, vol. 271, No. 3, 1994, pp. 1477-1482.

Korpela et al., "Lactobacillus rhamnosus GG shows antioxidative properties in vascular endothelial cell culture", *Milchwissenschaft*, 52(9), 1997, pp. 503-505.

Denariaz et al., "Immunity and Probiotics", entire manual, 1999.

Dugas et al., "Immunity and Probiotics", *Trends Immunology Today*, Sep. 1999, vol. 20 No. 9, pp. 1-4.

Isolauri, Erika, "Promotion of IgA Immune Response in Patients with Crohn's Disease by Oral Bacteriotherapy with *Lactobacillus GG*", *Ann Nutr Metab*, 1996, 40, pp. 137-145.

Isolauri, et al., "A Human *Lactobacillus* Strain (*Lactobacillus Casei* sp strain GG) Promotes Recovery From Acute Diarrhea in Children", *Pediatrics*, vol 88. No. 1, Jul. 1991, pp. 90-97.

Dugas et al., "Nitric oxide production by human monocytes: evidence for a role of CD23", *Immunology Today*, vol. 16, No. 12, 1995, pp. 574-580.

Danone World Newsletter, Oct. 1995.

Solis Pereyra et al., "Induction of Human Cytokines By Bacteria Used in Dairy Foods", *Nutrition Research*, vol. 13, 1993, pp. 1127-1140.

EP Communication for Application No. 00909291.7.

* cited by examiner

SELECTION AND USES OF LACTIC ACID BACTERIA STRAINS MODULATING NON-SPECIFIC IMMUNITY

FIELD OF THE INVENTION

The invention relates to the use of lactic acid bacteria as regulators of inflammation of the intestinal mucous membrane.

BACKGROUND OF THE INVENTION

Lactic acid bacteria are conventionally used for manufacturing fermented food products, in particular dairy products.

It has been reported that, besides their nutrient qualities, some of these food products exert beneficial effects on health; these properties have been the subject of particular interest for some decades, and many investigations have been carried out with the aim of confirming them and of defining more precisely the role played by lactic ferments.

It has thus been shown that some lactic acid bacteria, in particular among lactobacilli and bifidobacteria, improve immunity against infectious agents [PAUBERT-BRAQUET et al., Int. J. Immunother. 11, 153–161 (1995); KAILA et al., Dis. Child. 72, 51–53 (1995); HUDAULT et al. Appl. Environ. Microbiol. 63, 513–518 (1997)], and also have anti-tumour activity [HAYATSU et al. Cancer Lett. 73, 173–179 (1993); HOSONO et al. Agric. Biol. Chem. 54, 1639–1643 (1990); HOSODA et al. J. Dairy Sci. 75, 976–981 (1992)].

These effects have, in particular, been attributed to an action on the composition of the intestinal microflora, to the detriment of pathogenic microorganisms, and/or to a more direct action on the immune system, manifesting itself in particular through an increase in the level of cytokines which activate the immune system, such as γIFN of interleukins, and also an increase in the number of activated cells involved in the specific or non-specific immune response, such as lymphocytes and macrophages, and an increased secretion of immunoglobulins [PERDIGON et al., Int. J. Immunother. 9, 29–52, PORTIER et al., Int. J. Immunother. 9, 217–224 (1993); SOLIS PEREYRA and LEMONNIER, Nutr. Research 13, 1127–1140 (1993)]; DE SIMONE et al., Int. J. Immunother. 9, 23–28 20 (1993); PERDIGON et al., J. Dairy Res. 61, 553–562 (1994); SCHIFFRIN et al. J. Dairy Sci. 78, 491–497 (1995)].

However, it appears that the beneficial effects induced by lactic acid bacteria may vary depending on the origin of the pathological condition concerned, the bacterial species and/or strain used and the conditions of administration. In order to more successfully adapt the use of these bacteria, or of the products containing them, in the context of treating or of preventing specific pathological conditions, and in order to be in a position to select the bacteria which are the most suitable for the desired use, it is therefore necessary to more clearly understand the mechanisms by which their effects are exerted.

The inventors have undertaken to study the effect, on the intestinal mucous membrane, of lactic acid bacteria of the *Lactobacillus casei* group; with the same, they have chosen the *L. casei* strain DN 114001. This strain is described in PCT application WO 96/20607 in the name of: COMPAGNIE GERVAIS DANONE, and was deposited on 30 Dec. 1994, with the CNCM (Collection Nationale de Cultures de Microorganismes [National Collection of Microorganism Cultures]) held by the Institut Pasteur, 25 rue du Docteur Roux, in Paris, under the number I-1518, and the beneficial properties thereof in the context of treating diarrhoea have been shown.

The inventors have studied the effect, in vitro of this *L. casei* strain on the production of mediators of non-specific immunity (pro-inflammatory cytokines and nitric oxide), by enterocytes in culture.

These cell lines, which are derived from human intestinal epithelium, constitute a model for studying the response of the latter to an attack, which may be infectious or otherwise. This response manifests itself in particular through the production of pro-inflammatory cytokines (mainly IL-1, IL-6, TNF-α), and of nitric oxide (NO) generated by an inducible isoform of NO synthase (iNOS). Nitric oxide participates, through its antimicrobial properties, in the defence against pathogenic microorganisms and, when it is produced in a small amount, in the production of the intestinal mucous membrane. However, at high dose, it decreases the viability of the epithelial cells and contributes to the establishment and to the maintaining of a chronic inflammatory state [ALICAN and KUBES, Am. J. Physiol. 270, G225–237, (1996); TEPPERMAN et al., J. Pharmacol. Exp. Ther., 271, 1477–1482, (1994)]. The production of NO by enterocytes in culture can be induced with pro-inflammatory cytokines [VALETTE et al., Br. J. Pharmacol., 121, 187–182 (1997); KOLIOS et al., Br. J. Pharmacol., 116, 2866–2872 (1995)], and also with lipopolysaccharide (LPS) toxins of certain gram-negative bacteria (TEPPERMAN et al., 1994, abovementioned publication). Recent studies [SALZMAN et al., Gastroenterology, 114, 93–102, (1998); WITTHOFT et al., Am. J. Physiol., 275, G564–571, (1998)] indicate that *Escherichia coli, Salmonella dublin*, and *Shigella flexneri* enteropathogenic bacteria induce the expression of iNOS and the production of NO in enterocyte cultures which may or may not have been preactivated with pro-inflammatory cytokines.

The inventors have now noted that in the case of their experiments with *L. casei*, the action on the production of pro-inflammatory cytokines and of NO varies according to the activation state of the enterocytes. Specifically, when the cells are in their basal state, no effect of *L. casei* is observed; when they are activated by adding pro-inflammatory cytokines (which reproduces the conditions of an attack, which may be infectious or otherwise), a low production of NO and of TNF is observed; this response to the attack is very significantly increased by adding *L. casei*. Finally, in the case of cells hyperactivated by adding inflammatory cytokines and LPS (which reproduces the conditions of a pathogenic inflammatory state), a decrease in the production of NO and of TNF, which is restored to an optimum level, is, on the contrary, observed.

It appears, therefore, that this *L. casei* strain promotes an adaptive response of cells to an attack, via the modulation of factors involved in non-specific immunity.

SUMMARY OF THE INVENTION

The demonstration of these properties makes it possible to propose the use of the *L. casei* strain CNCM I-1518, and/or of any other lactic acid bacteria strain capable of decreasing the production of NO by cultures of enterocytes preactivated with pro-inflammatory cytokines and bacterial LPS, for producing compositions which regulate the inflammatory response of enterocytes, and in particular which inhibit a pathogenic inflammatory response.

Advantageously, use will be made of a strain which is also capable of increasing the production of NO by cultures of enterocytes preactivated with pro-inflammatory cytokines.

The compositions produced can be used for preventing or treating acute or chronic, inflammatory pathological conditions of the intestine (colitis, enteritis, Crohn's disease, haemorrhagic rectocolitis, etc.), whether or not these pathological conditions are of infectious origin (inducted by bacteria, viruses, yeasts, etc.); they are particularly suitable in the context of treating chronic inflammatory states.

In accordance with the invention, the lactic acid bacteria can be used in the form of whole bacteria which may or may not be living, in the form of a bacterial lysate or in the form of bacterial fractions; the bacterial fractions suitable for this use can be chosen by testing their properties of increasing the production of NO by cultures of enterocytes preactivated with pro-inflammatory cytokines, and of decreasing the production of NO by cultures of enterocytes preactivated with pro-inflammatory cytokines and bacterial LPS.

Preferably, these compositions can be administrated in the form of food supplements. They may in particular be fermented dairy products; in this case, the lactic acid bacteria used, in accordance with the invention, for producing these compositions can be part of the ferment used for producing these dairy products.

Use may in particular be made of lactic acid bacteria chosen from lactobacilli, lactococci, streptococci and bifidobacteria. Advantageously, an *L. casei* strain, and preferably the CNCM-I-1518 strain, is used.

Novel lactic acid bacteria strains which have properties which modulate non-specific immunity, and which can in particular be used for producing compositions which regulate the inflammatory response of enterocytes, can be obtained by carrying out a screening process comprising the selection of lactic acid bacteria strains capable of decreasing the production of NO by cultures of enterocytes preactivated with pro-inflammatory cytokines and bacterial LPS.

Advantageously, said process also comprises a step for selecting strains capable of increasing the production of NO by cultures of enterocytes preactivated with pro-inflammatory cytokines and, optionally, a step for selecting strains which exert no effect on the production of NO by non-activated enterocytes.

According to a preferred embodiment of the process in accordance with the invention, said strains are screened using cultures of lactic acid bacteria chosen from the group consisting of lactobacilli, lactococci, streptococci and bifidobacteria.

The invention also encompasses the foods and nutrient supplements, in particular the fermented dairy products, containing these novel strains, or products derived from the latter, in particular by cell lysis and/or fractionation.

DETAILED DESCRIPTION OF THE INVENTION

The present invention will be more clearly understood with the aid of the further description which follows, which refers to non-limiting examples illustrating the demonstration of the properties of the CNCM I-1518 strain.

GENERAL EXPERIMENTAL PROTOCOLS

The recombinant human cytokines (IL-1β, TNF-α, γ-IFN, $10^7$ U/mg) used originate from the company IMMUGENEX (Los Angeles, Calif.); the PDTC (inhibitor of the formation of the NFκ-B transcription factor), the L-NAME (NO-synthase inhibitor) and the *Escherichia coli* lipopolysaccharide originate from the company SIGMA (St Louis, Mo.).

The ELISA assay kits for the IL-1β and TNF-α cytokines originate from the company BIOSOURCE.

The total extracts of *L. casei*, used in the experiments, are obtained by sonication of suspensions of the CNCM I-1518 strain for 10 minutes in order to rupture the bacteria.

Culturing and Stimulation of Enterocytes

The 2 colon carcinoma cell lines HT29 and Caco-2 were used.

The HT29 line, initially isolated by FOGH and TREMPE (Human Tumor Cells *In Vitro*, 115–156, J. FOGH Ed, Plenum Press, New York, 1975) is available from the ATCC collection (Rockville USA), under the number ATCC HTB-38.

The Caco-2 line, initially isolated by FOGH (J. Natl. Cancer Inst. 58, 209–214, 1977) is available from the ATCC collection (Rockville USA), under the number ATCC HTB-37.

LEGENDS OF THE FIGURES

EXAMPLE 1

Effect of *L. casei* on the Production of Nitric Oxide by the Colon Epithelial Cell Lines Each of the 2 lines was seeded at $2 \times 10^5$ cells/well in 96-well plates, in DMEM medium supplemented with 5% of SVF, with 100 U/ml of penicillin, with 100 μg/ml of streptomycin and with 2 mM of L-glutamine.

The cells are pre-incubated for 24 hours at 37° C., 5% $CO_2$, in the presence of CYTOMIX (IL-1β: 10 ng/ml, TNF-α: 25 ng/ml and γ-IFN: $10^3$ U/ml mixture). The cells are then incubated for a further 24 hours in the presence or absence of increasing amounts of total extracts of *L. casei* (in % vol/vol).

After incubation, the culture supernatants are recovered and frozen, before determining the nitrite concentration. For certain experiments, L-NAME (1 mM), which is an analogue of L-arginine and constitutes a competitive inhibitor specific for NO-synthases, is added at the same time as the extracts of *L. casei*.

The amount of NO produced is evaluated by assaying, in the culture supernatants, the stable derivatives of this radical after reaction thereof in aqueous medium: the nitrites and nitrates. The nitrates are, initially, reduced to nitrites with bacteria expressing nitrate reductase, and the nitrites are then assayed using the GRIESS method. 100 µl of a solution composed of 1 volume of a solution of 1% sulphanilamide in 30% acetic acid, and of 1 volume of a solution of 0.1% N-1-naphthylethylenediamine dihydrochloride in 60% acetic acid, are added to 100 µl of supernatant. A standard calibration curve is prepared in the presence of various concentrations of sodium nitrite diluted in culture medium (DMEM 5% SVF). The absorbances are then determined at 540 nm using a MULTISCAN MCC340 reader (LAB-SYSTEM).

Figure 1:
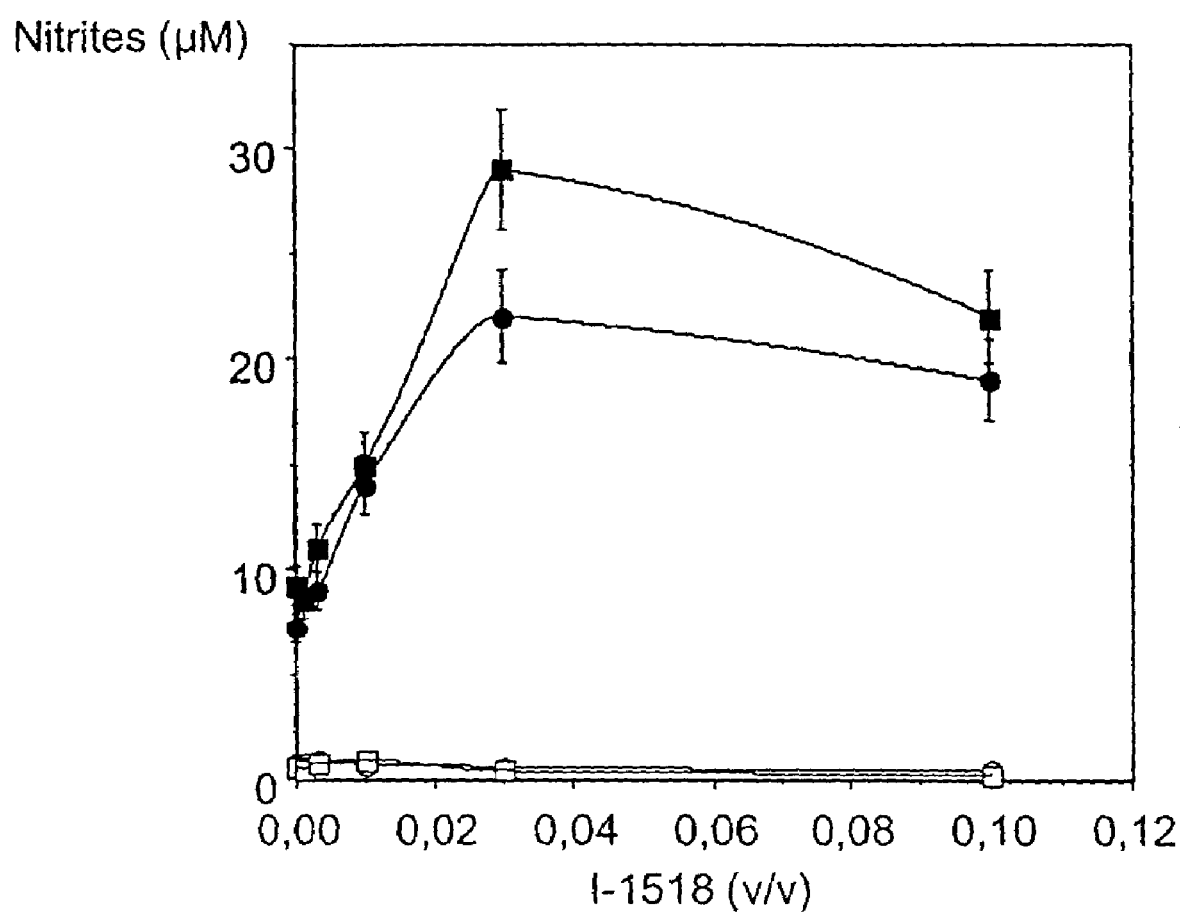
FIG. 1 represents the production of NO by the Caco-2 cells, preactivated (●) or not preactivated (○) with CYTOMIX or by the HT-29 cells, preactivated (■) or not preactivated (□) with CYTOMIX, in the presence of increasing amounts of total extract of the CNCM I-1518 strain.

FIG. 1 shows that, in the presence of CYTOMIX alone, only a limited production of NO by the HT-29 and Caco-2 lines is observed; this production is increased in a dose-dependent manner by adding the extract of L. casei. A maximum effect is observed for a concentration of approximately 3% (v/v) of extract of L. casei. In the absence of CYTOMIX, L. casei has no effect on the production of NO by either of the lines.

Figure 2:
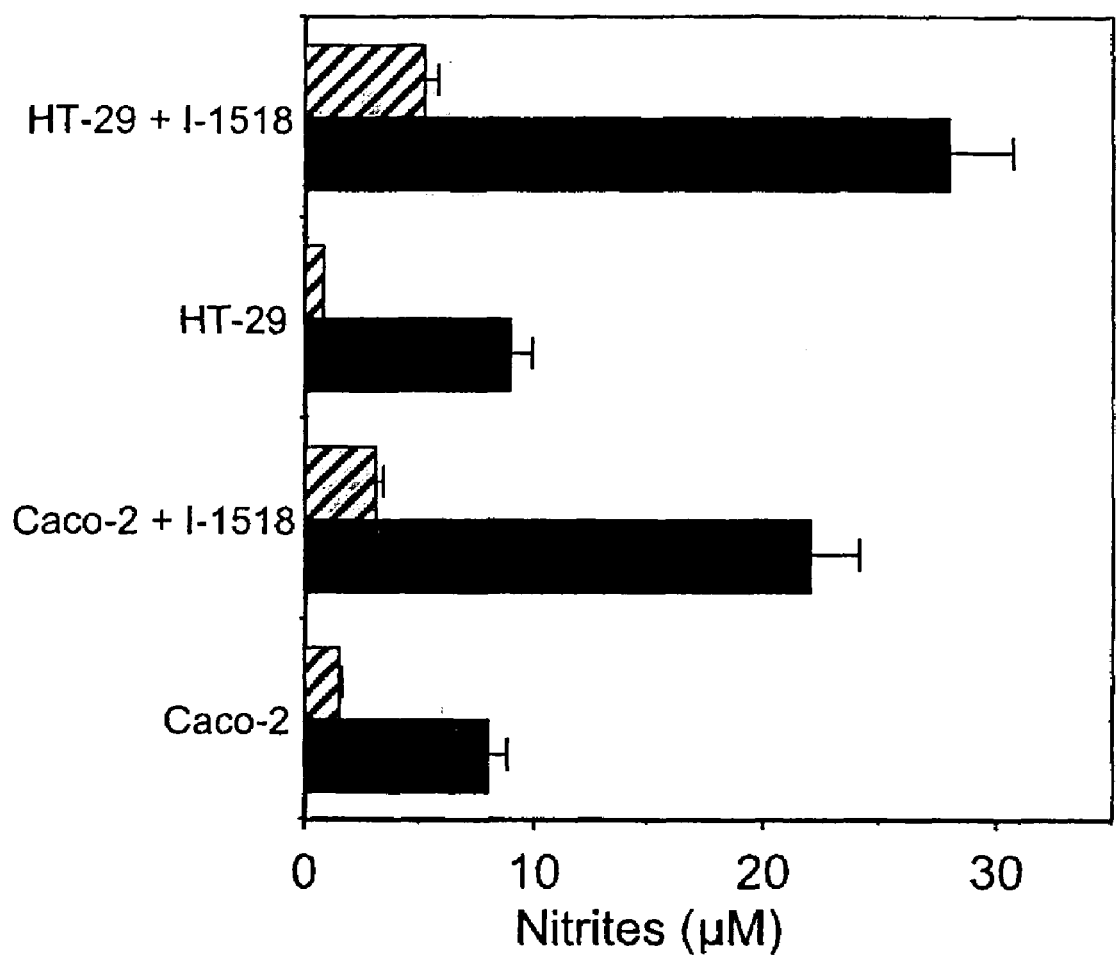
FIG. 2 represents the effect of L-NAME on the production of NO by the Caco-2 cells, or by the HT-29 cells, preactivated with CYTOMIX, in the presence or absence of total extract (3% v/v) of the CNCM I-1518 strain.▨■

FIG. 2 shows that this CYTOMIX-induced production is inhibited by adding L-NAME, in the presence or absence of total extract of L. casei (3% v/v).

EXAMPLE 2

Effect of L. casei on the Production of TNF-α by the Colon Epithelial Cell Lines Each of the 2 lines was seeded at $2 \times 10^6$ cells/well in 24-well plates, in DMEM medium supplemented with 5% of SVF, with 100 U/ml of penicillin, with 100 µg/ml of streptomycin and with 2 mM of L-glutamine. The cells are then incubated for 24 hours in the presence of CYTOMIX, and then for a further 24 hours in the presence of the total extracts of L. casei. For certain experiments, L-NAME (1 mM) or an inhibitor of the NFκB transduction pathway (PDTC: 10 pM) are added at the same time as the bacterial extracts.

The culture supernatants are then recovered and the cytokine concentration thereof is determined by ELISA.

Figure 3:
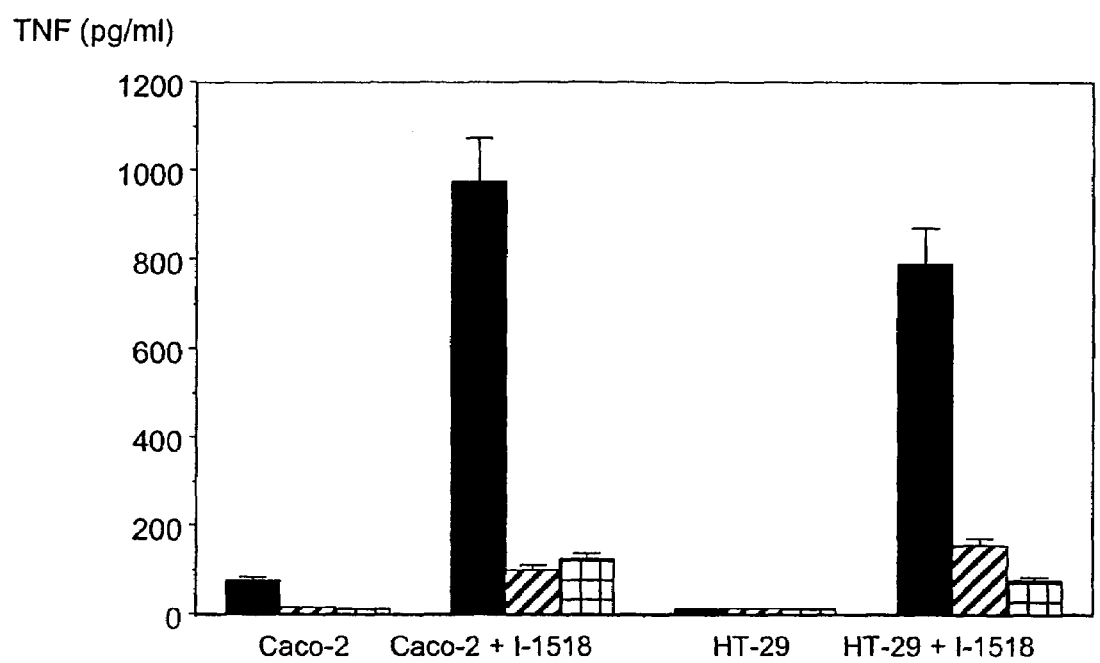
FIG. 3 represents the effect of L-NAME and of PDTC on the production of TNF by the Caco-2 cells, or by the HT-29 cells, preactivated with CYTOMIX, in the presence or absence of total extract (3% v/v) of the CNCM I-1518 strain.▨■⊞

FIG. 3 shows that, in the presence of CYTOMIX alone, there is only a low production of TNF-α by the Caco-2 line, and an absence of production of this cytokine by the HT-29 line. This production is greatly increased, for both lines, by adding total extract of L. casei; it is inhibited by adding L-NAME or PDTC, which shows that the activation of production of pro-inflammatory cytokines by L. casei involves the production of NO and the activation of NFκB.

The results given in Table 1 below show that the addition of L. casei to the cells preactivated with CYTOMIX also activates the production of IL-1β.

TABLE I

| Cell | Pre-activation | Stimulation | IL1-β (pg/ml) | TNF-α (pg/ml) |
|---|---|---|---|---|
| Caco-2 | none | none | ND | ND |
| Caco-2 | CYTOMIX | none | 150 ± 15 | 75 ± 11 |
| Caco-2 | none | CNCM I-1518 | 95 ± 8 | ND |
| Caco-2 | CYTOMIX | CNCM I-1518 | 1254 ± 55 | 975 ± 85 |
| HT-29 | none | none | ND | ND |
| HT-29 | CYTOMIX | none | ND | ND |
| HT-29 | none | CNCM I-1518 | ND | ND |
| HT-29 | CYTOMIX | CNCM I-1518 | 908 ± 63 | 789 ± 45 |

ND: NOT DETERMINED

EXAMPLE 3

Effect of L. casei, in the Presence of LPS from Gram⁻ Bacteria, on the Production of Nitric Oxide by the Colon Epithelial Cell Lines Preactivated with Pro-inflammatory Cytokines The protocol is identical to that of Example 1 above, with the only difference being that 10 µg/ml of E. coli LPS are added during the incubation with the total extract of L. casei.

Figure 4:
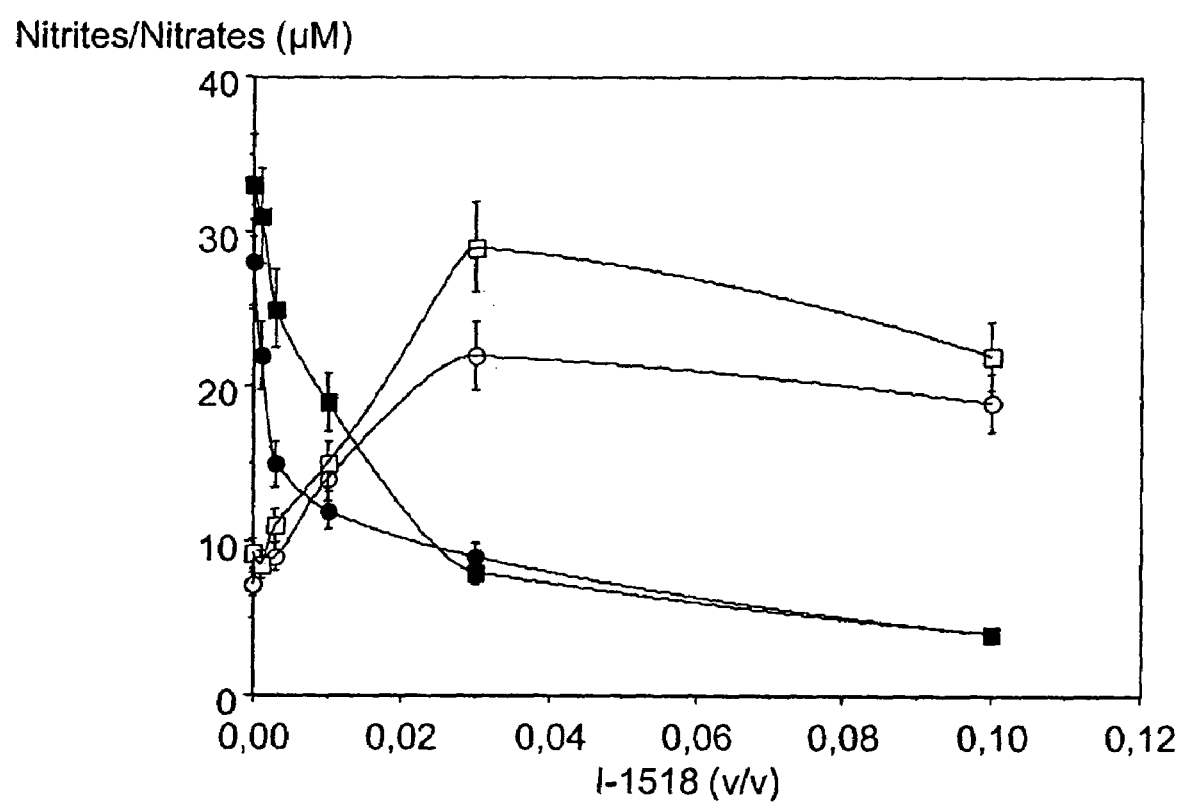
FIG. 4 represents the production of NO by the Caco-2 cells, preactivated with CYTOMIX alone (○) or with CYTOMIX+LPS (●), or with the HT-29 cells, preactivated with CYTOMIX alone (□) or with CYTOMIX+LPS (■), in the presence of increasing amounts of total extract of the CNCM I-1518 strain.

The results are illustrated in FIG. 4, which shows a considerable production of NO in the absence of L. casei (cells stimulated with CYTOMIX+LPS), which decreases in the presence of increasing amounts of L. casei, until returning to the level of that of the cells activated with the cytokines alone.

What is claimed is:

1. A method for regulating the inflammatory response of enterocytes, said method comprising contacting said enterocytes with a composition containing as an active agent a lactic acid bacteria strain capable of decreasing the production of nitric oxide (NO) by cultures of enterocytes preactivated with a mixture of pro-inflammatory cytokines comprising interleukin-β (IL-1β), Tumor Necrosis Factor-α (TNF-α) and interferon-γ (IFN-γ) and bacterial lipopolysaccharides (LPS).

2. A method according to claim 1, wherein said strain is also capable of increasing the production of NO by cultures of enterocytes preactivated with pro-inflammatory cytokines.

3. A method according to claim 1, wherein said bacterial strain is a Lactobacillus casei (L. casei) strain.

4. A method according to claim 1, wherein said bacterial strain is the L. casei strain CNCM I-1518.

5. A method according to claim 1, wherein said composition is in the form of a food supplement.

6. A method according to claim 1, wherein said composition is in the form of a fermented dairy product.

7. A method according to claim 1, wherein the lactic acid bacteria is in the form of whole bacteria which may or may not be living.

8. A method according to claim 1, wherein the lactic acid bacteria is in the form of a bacterial lysate.

9. A method according to claim 1, wherein the lactic acid bacteria is in the form of bacterial fractions.

* * * * *